United States Patent [19]

Iwasaki et al.

[11] Patent Number: 5,003,087
[45] Date of Patent: Mar. 26, 1991

[54] PROCESS FOR PREPARING A NAPHTHALENE DERIVATIVE AND A SYNTHETIC INTERMEDIATE THEREOF

[75] Inventors: Tameo Iwasaki, Nishinomiya; Hiroshi Ohmizu, Kyoto; Masami Takahashi, Takarazuka, all of Japan

[73] Assignee: Tanabe Seiyaku Co., Ltd., Osaka, Japan

[21] Appl. No.: 461,506

[22] Filed: Jan. 5, 1990

[30] Foreign Application Priority Data

Feb. 3, 1989 [JP] Japan .................................. 64-26416

[51] Int. Cl.$^5$ ..................... C07C 69/78; C07D 307/83
[52] U.S. Cl. .................................... 549/299; 549/298; 560/56; 556/438; 558/406
[58] Field of Search ....................... 549/299, 298, 214; 560/56; 558/406; 556/438

[56] References Cited

U.S. PATENT DOCUMENTS 4,728,740 3/1988 Vyas et al. .......................... 549/299
4,771,072 9/1988 Iwasaki et al. ...................... 549/599

Primary Examiner—Glennon H. Hollrah
Assistant Examiner—Mark W. Russell
Attorney, Agent, or Firm—Browdy and Neimark

[57] ABSTRACT

A novel process for preparing a naphthalene derivative of the formula:

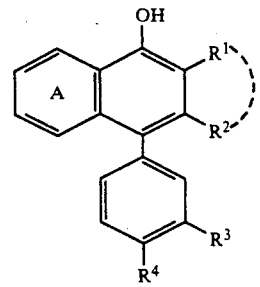

wherein $R^1$ and $R^2$ are a lower alkoxycarbonyl group or both may combine to form a group of the formula

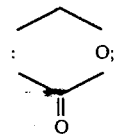

one of
$R^3$ and $R^4$ is hydrogen atom or a lower alkoxy group and the other is a lower alkoxy group; ring A is a substituted or unsubstituted benzene ring, which is useful as a hypolipidemic agent, and a novel intermediate of the formula:

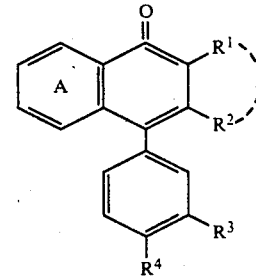

wherein R1, R2, R3, R4 and ring A are the same as defined above.

5 Claims, No Drawings

PROCESS FOR PREPARING A NAPHTHALENE DERIVATIVE AND A SYNTHETIC INTERMEDIATE THEREOF

The present invention relates to a process for preparing a naphthalene derivative which is useful as a hypolipidemic agent, and relates to a synthetic intermediate thereof.

Prior Art 1-(3- and/or 4-lower alkoxyphenyl)-2,3-bis(lower alkoxycarbonyl)-4-hydroxynaphthalene compounds and 1-(3- and/or 4-lower alkoxyphenyl)-3-hydroxymethyl-4-hydroxy-2-naphthoic acid lactone compounds are useful as a hypolipidemic agent.

Hitherto, it has been known that these compounds can be prepared by reacting 2-(α-hydroxy-3- and/or 4-lower alkoxybenzyl)benzaldehyde or di-lower alkyl acetal thereof with acetylenedicarboxylic acid di-lower alkyl ester and if necessary, by further subjecting the product to reductive lactonization [Japanese Patent First Publication (Kokai) No. 267541/1986].

DETAILED DESCRIPTION OF THE INVENTION

The present inventors have been studied intensively and accomplished a novel process for preparing a naphthalene derivative, wherein the synthetic route is completely different from those of the conventional methods.

According to the present invention, a naphthalene derivative of the formula:

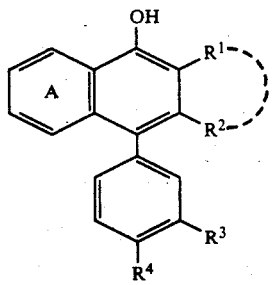

(I)

wherein $R^1$ and $R^2$ are a lower alkoxycarbonyl group or both may combine to form a group of the formula

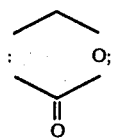

one of $R^3$ and $R^4$ is hydrogen atom or a lower alkoxy group and the other is a lower alkoxy group; ring A is a substituted or unsubstituted benzene ring, can be prepared by the steps of:

A. reacting the three compounds of the formulae:

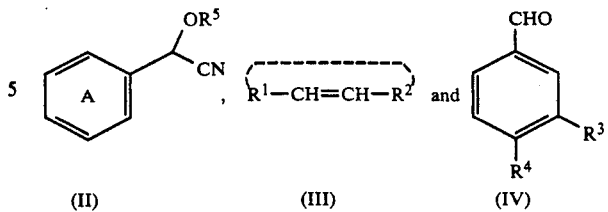

wherein $R^5$ is a protecting group for a hydroxy group and $R^1$, $R^2$, $R^3$, $R^4$ and ring A are the same as defined above, B. treating the product with an acid to give a protected-oxy-tetrahydronaphthalene compound of the formula:

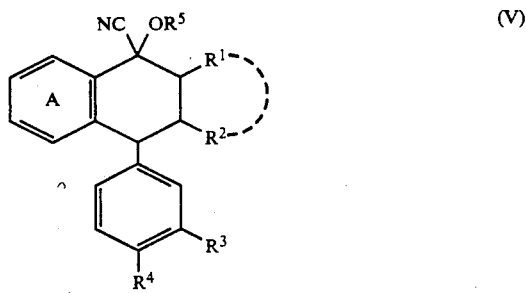

wherein $R^1$, $R^2$, $R^3$, $R^4$, $R^5$ and ring A are the same as defined above, C. treating the compound (V) or a salt thereof with a fluorine ion-donor to give an oxo-tetrahydronaphthalene compound of the formula:

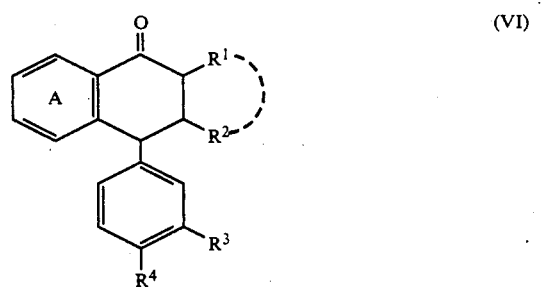

wherein $R^1$, $R^2$, $R^3$, $R^4$ and ring A are the same as defined above,

D. further oxidizing the compound (VI) or an enol-form tautomer thereof.

The reaction of the starting compounds (II), (III) and (IV) can be carried out in the presence of a basic substance. The basic substance may be any conventional basic substance, and it is more preferable to use lithium amides (e.g., lithium diisopropylamide), aryl lithiums (e.g., phenyl lithium) or alkyl lithiums (e.g., n-butyl lithium). The protecting groups ($R^5$) for a hydroxy group in a protected oxy-acetonitrile compound (II) may be any conventional protecting groups for hydroxy group, and it is more preferable to use a mono-, di- or tri-lower alkylsilyl group (e.g., methylsilyl group, dimethylsilyl group, trimethylsilyl group, tert.-butyldimethylsilyl group), a lower alkoxy-lower alkyl groups (e.g., methoxymethyl group), a lower alkoxy-lower alkoxy-lower alkyl groups (e.g., methoxyethoxymethyl group) or a phenyl lower alkyl groups (e.g., benzyl group). When $R^1$ and $R^2$ in a substituted ethylene compound (III) are a lower alkoxycarbonyl group, either cis- or trans-substituted compound thereof can be used. The reaction is preferably carried out with cooling, for example, at −78° C. to −40° C. The said reaction can be carried out in a suitable solvent. As a solvent, the conventional organic solvents, for example, tetrahydrofuran, ether, diglyme, hexane, toluene and xylene can be used. When the said reaction is carried out, it is preferred that an aldehyde compound (IV) is added into the reaction system after reacting a protected oxyacetonitrile compound (II) with a substituted ethylene compound (III).

The acid treatment of the product can be carried out in the conventional methods. As an acid, either organic acids or inorganic acids can be used, especially it is preferred to use organic acids (e.g., trifluoroacetic acid, methanesulfonic acid, toluenesulfonic acid). The acid treatment can be carried out at room temperature or with heating, for example, at 10° C. to 50° C. The said reaction can be carried out in a suitable solvent, and as a solvent, it is preferred to use the same solvents as those used in the above reaction of three compounds (II), (III) and (IV).

The subsequent treatment of a protected oxy-tetrahydronaphthalene compound (V) or a salt thereof with a fluorine ion-donor can be carried out in the conventional methods. As a fluorine ion-donor, any conventional one can be used, and it is preferred to use a mixture of a fluoride and an acid. The fluoride includes alkali metal fluorides (e.g., potassium fluoride), ammonium fluoride, and tetra(lower)alkylammonium fluorides (e.g., tetramethylammonium fluoride, tetrabutylammonium fluoride), and the acid includes, for example, acetic acid, trifluoroacetic acid, methanesulfonic acid, toluenesulfonic acid. The preferred fluorine ion-donor includes also hydrogen fluoride and the like. The said reaction can be carried out effectively at ambient temperature in a suitable solvent. The solvent includes any conventional organic solvents, for example, methylene chloride or chloroform.

The oxidation reaction of thus obtained oxo-tetrahydronaphthalene compound (VI) or an enol-form tautomer thereof can be carried out in the conventional method. The said oxidation reaction can be carried out by treating the compound (VI) or a tautomer thereof with an oxidizing agent or treating with a base after treating with a halogenating agent. The conventional oxidizing agents can be used and it is preferred to use selenium dioxide, 2,3-dichloro-4,5-dicyanobenzoquinone, oxygen gas, or air. On the other hand, the conventional halogenating agents can be used as the halogenating agent and it is preferred to use transition metal bromides (e.g., cupric bromide) in the presence of alkali metal bromides (e.g., lithium bromide, sodium bromide). Either organic bases or inorganic bases can be used as the base and it is preferred to use triethylamine, tributylamine, 1,8-diazabicyclo[5.4.0]undec-7-ene, alkali metal hydroxide or alkali metal carbonate. The oxidation reaction of the compound (VI) can be carried out under ice cooling or with heating depending on the oxidizing method to be employed. The reaction using a halogenating agent can be carried out with heating, especially at 50° C. to 80° C., and the subsequent treatment with a base can be carried out under cooling or at ambient temperature, for example, at 0° C. to 25° C. Both reactions are preferably carried out in a suitable solvent. The solvent includes any conventional organic solvents, for example, acetonitrile, propionitrile and chloroform.

In the above reactions, the salts employed for the starting compound (II) wherein ring A is a benzene ring substituted by hydroxy group, for the intermediates (V) and (VI), and for the enol-form tautomer of the intermediate (VI) may be alkali metal salts, alkaline earth metal salts and the like. These salts can be used in the reactions in the same manner as the corresponding free form of the compound.

The intermediates (V) and (VI) may have diastereoisomers due to 4 and 3 asymmetric carbons thereof respectively, and any isomer or a mixture thereof can be used in the process of the present invention.

According to the process of the present invention, naphthalene derivatives disclosed in Japanese Patent Publication (Kokai) No. 267541/1986 can advantageously be prepared on an industrial scale without regard to the kind of ring A thereof. For example, the compound (I) wherein ring A is an unsubstituted benzene ring, a benzene ring substituted by a lower alkylenedioxy group or a benzene ring having 1 -3 substituents selected from the group consisting of a lower alkoxy group, a lower alkyl group, a phenyl-lower alkoxy group, hydroxy group and a halogen atom, and the naphthalene derivative (I) wherein $R^1$ and $R^2$ are a lower alkoxycarbonyl group, $R^3$ and $R^4$ are a lower alkoxy group, ring A is a substituted benzene ring of the formula:

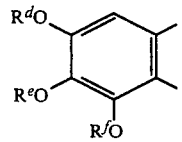

wherein $R^d$, $R^e$ and $R^f$ are a lower alkyl group, can advantageously be prepared.

The naphthalene derivative (I) thus obtained may optionally be converted into a pharmaceutically acceptable salt thereof by treating properly with an alkali metal hydride, an alkali metal hydroxide, an alkaline earth metal hydroxide, quaternary ammonium hydroxide and like.

The process of the present invention proceeds by a novel reaction wherein the synthetic route is completely different from those of the conventional processes. The process of the present invention has an industrially advantage that the intermediate; oxy-tetrahydronaphthalene compound (V) can be prepared by reacting the three starting compounds (II), (III) and (IV) in a single procedure so that a naphthalene derivative being useful as a hypolipidemic agent can be obtained in a simple reaction procedure.

The oxo-tetrahydronaphthalene compound (VI) which is obtained as an intermediate in the present invention is in equilibrium with an enol-form tautomer thereof in a solvent as described in the following formulae:

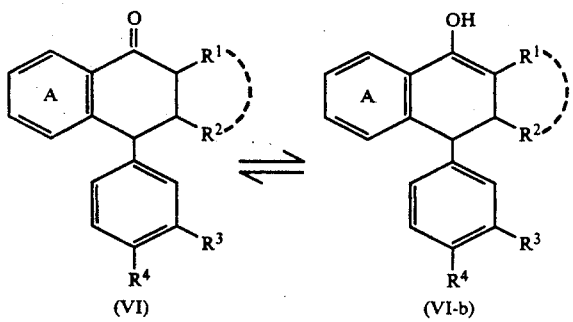

wherein $R^1$, $R^2$, $R^3$, $R^4$ and ring A are the same as defined above, and both can be used in the present invention.

The intermediates (VI) are novel compounds except a compound wherein ring A is a benzene group substituted by a lower alkylenedioxy group, and $R^1$ and $R^2$ combine to form a group of the formula;

and $R^3$ and $R^4$ are lower alkoxy group.

The starting compound (II) of the present invention can be prepared by reacting a benzaldehyde compound of the formula:

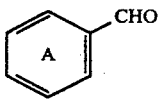 (VII)

wherein ring A is the same as defined above, with an alkali metal cyanide and a compound of the formula:

$R^5-X$ (VIII)

wherein X is a halogen atom and $R^5$ is the same as defined above, in the presence of a Lewis acid (e.g., zinc (II) iodide).

The present invention is illustrated by the following Examples but should not be construed to be limited thereto.

EXAMPLE 1

(1-a) 3,4,5-Trimethoxybenzaldehyde (50 g) is dissolved in acetonitrile (prepared by distillation with phosphorus pentoxide) (250 ml). To this solution are added potassium cyanide (24.9 g), zinc (II) iodide (8.1 g) and tert.-butyldimethylsilyl chloride (46.1 g) and the mixture is stirred at room temperature overnight. Acetonitrile is distilled off from the reaction mixture and to the residue is added diethyl ether and the insoluble materials are filtered off. The filtrate is washed with water, dried and concentrated under reduced pressure. The resulting residue is purified by silica gel column chromatography [solvent: n-hexane/ethyl acetate (3:1)] and crystallized from a mixture of n-hexane and isopropyl ether to give (3,4,5-trimethoxyphenyl)(tert.-butyldimethylsilyloxy)acetonitrile (67 g) as colorless crystal.
Yield: 78%
M.p.: 43° C.

(1-b) 3,4,5-Trimethoxybenzaldehyde, acetonitrile, potassium cyanide, zinc (II) iodide and trimethylsilyl chloride are treated in the same manners as in the above procedure (1-a) to give (3,4,5-trimethoxyphenyl)(trimethylsilyloxy)acetonitrile as oily product.
B.p.: 145°–147° C. (1 mmHg)

(2-a) To lithium diisopropylamide solution [prepared from a solution of diisopropylamine (3.0 g) in tetrahydrofuran (50 ml) and 1.6M n-butyl lithium solution (20.4 ml) in n-hexane under dry ice cooling] is added dropwise a solution of the product (10 g) obtained in the above procedure (1-a) in tetrahydrofuran (20 ml) at −70° C. and the mixture is stirred at the same temperature for about 5 minutes. To this mixture is added dropwise a solution of maleic acid dimethyl ester (4.27 g) in tetrahydrofuran (50 ml) over the period of about 20 minutes. Further, to this mixture is added dropwise a solution of 3,4-dimethoxybenzaldehyde (4.93 g) in tetrahydrofuran (20 ml) and then a mixture of acetic acid (3.7 ml) and water (50 ml) is added to the reaction mixture. The mixture is extracted with ethyl acetate at room temperature. The extract is washed with water and dried. The solvent is distilled off and the resulting residue is purified by silica gel column chromatography [solvent: n-hexane/ethyl acetate (2:1)]. The eluate is concentrated and the residue is dissolved in acetic anhydride (20 ml) and stirred at room temperature for 2 hours. Further, trifluoroacetic acid (10 ml) is added to the mixture and allowed to stand overnight. The reaction solution is concentrated and the residue is extracted with chloroform. The extract is washed, dried and then the solvent is distilled off. The residue is crystallized from isopropyl ether and the insoluble materials are filtered off to give r-1-(3,4-dimethoxyphenyl)-t-2-methoxycarbonyl-c-3-methoxycarbonyl-4-cyano-4-(tert.-butyldimethylsilyloxy)-6,7,8-trimethoxy-1,2,3,4-tetrahydronaphthalene (12.9 g) as colorless crystal.
Yield: 69%
M.p.: 162°–163° C.

(2-b) The product obtained in the above procedure (1-b), maleic acid dimethyl ester and 3,4-dimethoxybenzaldehyde are treated in the same manners as in the above procedure (2-a) to give r-1-(3,4-dimethyoxyphenyl)-t-2-methoxycarbonyl-c-3-methoxycarbonyl-4-cyano-4-(trimethylsilyloxy)-6,7,8-trimethoxy-1,2,3,4-tetrahydronaphthalene as oily product.

(3-a) The product (10.1 g) obtained in the above procedure (2-a) is dissolved in methylene chloride (100 ml). To this solution are added tetra-n-butylammonium fluoride solution (17 ml) and acetic acid (1.2 ml) and the mixture is stirred at room temperature for 2 hours. The reaction solution is washed with water, dried and then the solvent is distilled off. The residue is purified by silica gel column chromatography [solvent: n-hexane/ethyl acetate (2:1)]. The eluate is concentrated and the resulting residue is crystallized from diethyl ether to give r-1-(3,4-dimethoxyphenyl)-t-2-methoxycarbonyl-3-methoxycarbonyl-4-hydroxy-6,7,8-trimethoxy-1,2-dihydronaphthalene (2.1 g) as colorless crystal.
Yield: 27%
M.p.: 132°–134° C.
NMR (CDCl$_3$, δ): 3.4–4.0 (m, 23H), 4.5 (d, 1H, J=2 Hz), 6.5–7.0 (m, 4H)

This product is in the form of equilibrium mixture with r-1-(3,4-dimethoxyphenyl)-t-2-methoxycarbonyl-c-3-methoxycarbonyl-4-oxo-6,7,8-trimethoxy-1,2,3,4-tetrahydronaphthalene in a solvent.

r-1-(3,4-Dimethoxyphenyl)-t-2-methoxycarbonyl-c-3-methoxycarbonyl-4-oxo-6,7,8-trimethoxy-1,2,3,4-tetrahydronaphthalene (4.8 g) is obtained as syrup by further concentrating the mother liquid.

Yield: 61%

(3-b) The product obtained in the above procedure (2-b) is treated in the same manners as in the procedure (3-a) to give r-1-(3,4-dimethoxyphenyl)-t-2-methoxycarbonyl-c-3-methoxycarbonyl-4-oxo-6,7,8-trimethoxy-1,2,3,4-tetrahydronaphthalene.

The physicochemical properties of this product are the same as those of the product obtained in the above procedure (3-a).

(4) A mixture of the product (2.0 g) obtained in the above procedure (3-a) or (3-b) (4-oxo compound), cupric bromide (1.83 g), lithium bromide (356 mg) and acetonitrile (50 ml) is refluxed with heating for 4 hours. Acetonitrile is distilled off from the reaction solution, and chloroform is added to the residue. The mixture is purified by silica gel column chromatography [solvent: chloroform/ethyl acetate (1:1)]. The eluate is concentrated and the residue is dissolved in chloroform and then triethylamine (10 ml) is added thereto. The mixture is allowed to stand at room temperature for 1 hour. The solution is acidified with conc. hydrochloric acid and the chloroform layer is collected. The chloroform layer is washed with water, dried and then the solvent is distilled off. Methanol is added to the residue and the precipitated crystal is collected by filtration to give 1-(3,4-dimethoxyphenyl)-2,3-bis(methoxycarbonyl)-4-hydroxy-6,7,8-trimethoxynaphthalene (1.1 g) as colorless prisms.

Yield: 55%

M.p.: 178°–179° C.

(5) A solution of the product (4.86 g) obtained in the above procedure (4) in tetrahydrofuran (100 ml) is added to a solution of 62.5% sodium hydride (0.387 g) in tetrahydrofuran (10 ml) with stirring at room temperature and the mixture is stirred at the same temperature for 1 hour. After the reaction, the solvent is distilled off under reduced pressure at a temperature under 30° C. The resulting residue is powdered with petroleum ether to give 1-(3,4-dimethoxyphenyl)-2,3-bis(methoxycarbonyl)-4-hydroxy-6,7,8-trimethoxynaphthalene sodium salt (4.8 g) as powder.

Ir $\nu_{Max}^{KBr}$ (cm$^{-1}$): 1710, 1680, 1600

EXAMPLE 2

(1) A solution of (3,4,5-trimethoxyphenyl)(tert.-butyldimethylsilyloxy)acetonitrile (10 g) in tetrahydrofuran (20 ml) is added dropwise to a lithium diisopropylamide solution [prepared from a solution of diisopropylamine (3.0 g) in tetrahydrofuran (50 ml) and 1.6M n-butyl lithium solution (2.04 ml) in n-hexane under dry ice cooling] at −70° C. The mixture is stirred at the same temperature for about 5 minutes, and thereto is added dropwise a solution of 2-oxo-2,5-dihydrofuran (2.49 g) in tetrahydrofuran (50 ml) over the period of about 20 minutes. Further, a solution of 3,4-dimethoxybenzaldehyde (4.93 g) in tetrahydrofuran (20 ml) is added thereto. A mixture of acetic acid (3.7 ml) and water (50 ml) is added to the reaction mixture and extracted with ethyl acetate at room temperature. The extract is washed with water, dried and the solvent is distilled off. The resulting residue is dissolved in methylene chloride (20 ml) and thereto is added trifluoroacetic acid. The mixture is allowed to stand at room temperature overnight. The reaction solution is diluted with methylene chloride and washed with water, and then the solvent is distilled off. The residue is purified by silica gel column chromatography (solvent: chloroform). The syrup obtained from the eluate is crystallized from isopropyl ether to give r-1-(3,4-dimethoxyphenyl)-c-3-hydroxymethyl-4-cyano-4-(tert.-butyl-dimethylsilyloxy)-6,7,8-trimethoxy-1,2,3,4-tetrahydronaphthalene-t-2-carboxylic acid lactone (12.7 g) as colorless crystal.

Yield: 75%

M.p.: 132°–135° C.

(2) The product (5.0 g) obtained in the above procedure (1) is dissolved in methylene chloride (50 ml). To the solution are added 1M tetra-n-butylammonium fluoride (10.5 ml) and acetic acid (791 mg) and the mixture is stirred at room temperature for 5 minutes. The reaction solution is washed with water, dried and then the solvent is distilled off. The resulting residue is dissolved in diethyl ether and cooled with ice. The precipitated crystal is collected by filtration to give r-1-(3,4-dimethoxyphenyl)-c-3-hydroxymethyl-4-oxo-6,7,8-trimethoxy-1,2,3,4-tetrahydronaphthalene-t-2-carboxylic acid lactone (2.33 g) as colorless crystal.

Yield: 62%

(3) A mixture of the product (1.0 g) obtained in the above procedure (2), cupric bromide (1.04 g), lithium bromide (203 mg) and acetonitrile (25 ml) is refluxed with heating for 8 hours. Acetonitrile is distilled off from the reaction solution and chloroform is added to the residue and further purified by silica gel column chromatography [solvent: chloroform/ethyl acetate (1:1)]. The eluate is concentrated and the residue is dissolved in chloroform. Trimethylamine (5 ml) is added thereto with ice cooling and the mixture is allowed to stand at room temperature for 1 hour. The solution is acidified with conc. hydrochloric acid and the chloroform layer is collected. The chloroform layer is washed with water, dried and then the solvent is distilled off. The resulting residue is dissolved in methanol and cooled with ice. The precipitated crystal is collected by filtration to give 1-(3,4-dimethoxyphenyl)-3-hydroxymethyl-4-hydroxy-6,7,8-trimethoxy-2-naphthoic acid lactone (520 mg) as colorless crystal.

Yield: 54%

M.p.: 261° C. (decomposed)

EXAMPLES 3 AND 4

(1) The corresponding starting compounds are treated in the same manners as in Example 1-(1-a) to give the compounds in the following Table 1.

TABLE 1

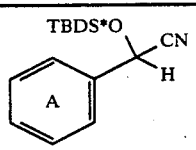

| Ex. No. | Ring A | Physicochemical Properties |
|---|---|---|
| 3-(1) | CH₃O-/CH₃O- substituted ring | M.p.: 54–55° C. Yield: 91% |

TABLE 1-continued

[Structure: Ring A with TBDS*O, CN, H substituents]

| Ex. No. | Ring A | Physicochemical Properties |
|---|---|---|
| 4-(1) | [methylenedioxyphenyl] | Oily product<br>Yield: 78%<br>NMR(CDCl$_3$, δ): 0.12(s, 3H),<br>0.20(s, 3H), 0.92(s, 9H),<br>5.33(s, 1H), 5.95(s 2H),<br>6.7-7.0(m, 3H) |

*TBDS means a group of the formula:

$(CH_3)_3C-\underset{\underset{CH_3}{|}}{\overset{\overset{CH_3}{|}}{Si}}-$ (the same, hereinafter)

(2) The products in the above procedure (1) are treated in the same manners as in Example 1-(2-a) to give the compounds of the following Table 2.

TABLE 2

[Structure: naphthalene with TBDS*O, CN, CO$_2$CH$_3$ groups and dimethoxyphenyl] (Note 1)

| Ex. No. | Ring A | Physicochemical Properties |
|---|---|---|
| 3-(2) | CH$_3$O, CH$_3$O-phenyl | Yield: 72%<br>NMR(CDCl$_3$, δ): 0.0-0.5(m,<br>6H), 1.8-2.0(m, 9H), 3.4-4.0<br>(m, 20H), 4.2-4.6(m,<br>1H), 6.2-7.2(m, 5H) |
| 4-(2) | [methylenedioxyphenyl] | Yield: 73%<br>NMR(CDCl3, δ): 0.0-0.6(m,<br>6H), 0.8-1.2(m, 9H), 3.5-4.2<br>(m, 14H), 4.3-4.6(m,<br>1H), 5.9-6.1(br, 2H), 6.2-7.4<br>(m, 5H) |

Note 1:
r-1-(3,4-Dimethoxyphenyl)-t-2-methoxycarbonyl-c-3-methoxycarbonyl compound (the same, hereinafter)

(3) The products in the above procedure (2) are treated in the same manners as in Example 1-(3-a) to give the compounds of the following Table 3.

TABLE 3

[Structure: tetralone with CO$_2$CH$_3$ groups and dimethoxyphenyl] (Note 1)

| Ex. No. | Ring A | Physicochemical Properties |
|---|---|---|
| 3-(3) | CH$_3$O, CH$_3$O-phenyl | Yield: 76%<br>NMR(CDCl$_3$, δ): 3.5-4.0(m,<br>20H), 4.3-4.7(m, 1H), 6.3-7.6<br>(m, 5H), |
| 4-(3) | [methylenedioxyphenyl] | Yield: 70%<br>NMR(CDCl3, δ): 3.6-4.0(m,<br>14H), 4.51(d, 1H, J = 1.5<br>Hz), 5.96(s, 2H), 6.2-7.5<br>(m, 5H) |

(4) The products in the above procedure (3) are treated in the same manners as in Example 1-(4) to give the compounds of the following Table 4.

TABLE 4

[Structure: naphthol with OH, CO$_2$CH$_3$ groups and dimethoxyphenyl]

| Ex. No. | Ring A | Physicochemical Properties |
|---|---|---|
| 3-(4) | CH$_3$O, CH$_3$O-phenyl | Colorless crystal<br>M.p.: 208-209° C.<br>Yield: 52% |
| 4-(4) | [methylenedioxyphenyl] | Colorless crystal<br>M.p.: 130-133° C.<br>Yield: 49% |

EXAMPLES 5 AND 6

(1) The corresponding starting compounds are treated in the same manners as in Example 2-(1) to give the compounds of the following Table 5.

TABLE 5

| Ex. No. | Ring A | Physicochemical Properties |
|---|---|---|
| 5-(1) | 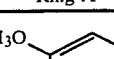 CH₃O, CH₃O | M.p.: 167–168° C. Yield: 69% |
| 6-(1) |  | Syrup Yield: 82% NMR(CDCl₃, δ): 0.1–0.5(m, 6H), 2.6–3.3(m, 2H), 3.7–4.1 (m, 6H), 4.1–4.6(m, 3H), 5.9–6.1(m, 2H), 6.6–7.3 (m, 5H) |

Note 2:
r-1-(3,4-Dimethoxyphenyl)-c-3-hydroxymethyl-t-2-carboxylic acid lactone compound (2) The products in the above procedure (1) are treated in the same manners as in Example 2-(2) to give the compounds of the following Table 6.

TABLE 6

| Ex. No. | Ring A | Physicochemical Properties |
|---|---|---|
| 5-(2) | CH₃O, CH₃O | Yield: 60% NMR(CDCl₃+ CF₃COOH, δ): 3.0–3.8(m, 2H), 3.82(s, 3H), 3.88(s, 3H), 3.94(s, 3H), 3.98(s, 3H), 4.1–4.8(m, 3H), 6.4(s, 1H), 6.6–7.0 (m, 3H), 7.5(s, 1H) |
| 6-(2) | (methylenedioxyphenyl) | Yield: 78% NMR(CDCl3, δ): 3.17(s, 3H), 2.9–3.6(m, 3H), 3.82(s, 9H), 3.91(m, 3H), 4.2–4.7 (m, 3H), 6.5–6.9(m, 3H), 7.27(s, 1H) |

(3) The products in the above procedure (2) are treated in the same manners as in Example 2-(3) to give the compounds of the following Table 7.

TABLE 7

| Ex. No. | Ring A | Physicochemical Properties |
|---|---|---|
| 5-(3) | CH₃O, CH₃O | Colorless crystal M.p.: 278° C. (decomposed) Yield: 48% |
| 6-(3) | (methylenedioxyphenyl) | Colorless crystal M.p.: 256° C. (decomposed) Yield: 51% |

EXAMPLES 7–23

The corresponding starting compounds are treated in the same manners as in Example 1 to give the compounds of the following Tables 8 and 9.

TABLE 8

| Ex. No. | Ring A | R³/R⁴ | Physicochemical Properties |
|---|---|---|---|
| 7 |  | $R^3 = -OCH_3$ $R^4 = -OCH_3$ | Colorless crystal M.p.: 182–184° C. |
| 8 | CH₃O | Same as above | Colorless crystal M.p.: 178–179° C. |
| 9 | CH₃O (para) | Same as above | Colorless crystal M.p.: 199–200° C. |
| 10 | CH₃O, Bzl*O | Same as above | Colorless crystal M.p.: 172–174° C. |
| 11 | CH₃O, HO | Same as above | M.p.: 231° C. (decomp.) |

TABLE 8-continued

Structure:
Naphthalene with OH, CO₂CH₃, CO₂CH₃, and phenyl substituted with R³ (meta) and R⁴ (para); Ring A fused.

| Ex. No. | Ring A | R³/R⁴ | Physicochemical Properties |
|---|---|---|---|
| 12 | 2,3-dichlorophenyl | R³ = —OCH₃<br>R⁴ = —OCH₃ | Colorless prisms<br>M.p.: 209–210° C. |
| 13 | 2,3-(ethylenedioxy)phenyl | Same as above | Light yellow crystal<br>M.p.: 228–229° C. |
| 14 | 3,4,5-trimethoxyphenyl (CH₃O, CH₃O, CH₃O) | R³ = —OC₂H₅<br>R⁴ = —OC₂H₅ | Colorless crystal<br>M.p.: 138–140° C. |
| 15 | Same as above | R³ = —O-nC₃H₇<br>R⁴ = —O-nC₃H₇ | Colorless needles<br>M.p.: 132° C. |
| 16 | Same above | R³ = —OC₂H₅<br>R⁴ = —CH₃ | Colorless needles<br>M.p.: 158° C. |
| 17 | Same as above | R³ = —OCH₃<br>R⁴ = —OC₂H₅ | Colorless needles<br>M.p.: 159° C. |
| 18 | methylenedioxyphenyl | R³ = —OC₂H₅<br>R⁴ = —OC₂H₅ | Colorless crystal<br>M.p.: 158–159° C. |
| 19 | Same as above | R³ = —OCH₃<br>R⁴ = —H | M.p.: 152–154° C. |
| 20 | Same as above | R³ = —H<br>R⁴ = —OCH₃ | Colorless crystal<br>M.p.: 169–171° C. |

Bzl means a benzyl group.

TABLE 9

Structure:
Naphthalene with OH, CO₂C₂H₅, CO₂C₂H₅, and phenyl substituted with R³ and R⁴; Ring A fused.

| Ex. No. | Ring A | R³/R⁴ | Physicochemical Properties |
|---|---|---|---|
| 21 | 3,4,5-trimethoxyphenyl (CH₃O, CH₃O, CH₃O) | R³ = —OCH₃<br>R⁴ = —OCH₃ | Colorless crystal<br>M.p.: 138–140° C. |
| 22 | methylenedioxyphenyl | R³ = —OC₂H₅<br>R⁴ = —OC₂H₅ | Colorless crystal<br>M.p.: 150–151° C. |
| 23 | Same as above | R³ = —O-iC₃H₇<br>R⁴ = O-iC₃H₇ | M.p.: 123–124° C. |

EXAMPLES 24–36

The corresponding starting compounds are treated in the same manners as in Example 2 to give the compounds of the following Table 10.

TABLE 10

Structure: naphthalene-fused lactone with OH, Ring A, phenyl with R³ and R⁴.

| Ex. No. | Ring A | R³/R⁴ | Physicochemical Properties |
|---|---|---|---|
| 24 | phenyl | R³ = —OCH₃<br>R⁴ = —OCH₃ | Colorless crystal<br>M.p.: 260° C. (decomp.) |
| 25 | 4-methoxyphenyl (CH₃O) | Same as above | Colorless crystal<br>M.p.: 254° C. (decomp.) |
| 26 | 3-methoxyphenyl (CH₃O) | Same as above | Colorless needles<br>M.p.: 234–236° C. |

TABLE 10-continued

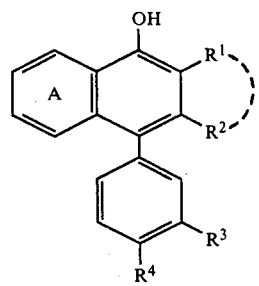

| Ex. No. | Ring A | R³/R⁴ | Physicochemical Properties |
|---|---|---|---|
| 27 | CH₃O-, BzlO- substituted benzene | Same as above | Colorless crystal M.p.: 243° C. (decomp.) |
| 28 | CH₃O-, OH- substituted benzene | Same as above | Colorless fine crystal M.p.: >270° C. (decomp.) |
| 29 | methylenedioxy benzene | Same as above | Yellow crystal M.p.: 273° C. (decomp.) |
| 30 | Cl, Cl substituted benzene | Same as above | Colorless crystal M.p.: 260° C. (decomp.) |
| 31 | CH₃O, CH₃O, CH₃O substituted benzene | R³ = —OC₂H₅ R⁴ = —OC₂H₅ | Colorless crystal M.p.: 219° C. (decomp.) |
| 32 | Same as above | R³ = —O-nC₃H₇ R⁴ = —O-nC₃H₇ | Colorless needles M.p.: 129–132° C. |
| 33 | methylenedioxy benzene | R³ = —OC₂H₅ R⁴ = —OC₂H₅ | Colorless needles M.p.: 251° C. (decomp.) |
| 34 | Same as above | R³ = —OCH₃ R⁴ = —H | M.p.: 275° C. (decomp.) |
| 35 | Same as above | R³ = —H R⁴ = —OCH₃ | Colorless crystal M.p.: 297° C. (decomp.) |
| 36 | Same as above | R³ = —O-iC₃H₇ R⁴ = —iC₃H₇ | M.p.: 223° C. |

What is claimed is:

1. A process for preparing a naphthalene derivative of the formula:

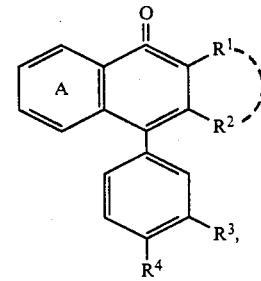

wherein R¹ and R² are a lower alkoxycarbonyl group or both may combine to form a group of the formula

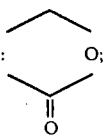

one of R³ and R⁴ is hydrogen atom or a lower alkoxy group and the other is a lower alkoxy group; ring A is a substituted or unsubstituted benzene ring, or a pharmaceutically acceptable salt thereof, which comprises the steps of:

A. oxidizing an oxo-tetrahydronaphthalene compound of the formula:

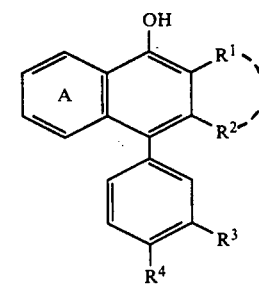

wherein R¹, R², R³, R⁴ and ring A are the same as defined above, an enol-form tautomer thereof or a salt thereof, B. if required, further converting the product into a pharmaceutically acceptable salt thereof.

2. A process for preparing a naphthalene derivative of the formula:

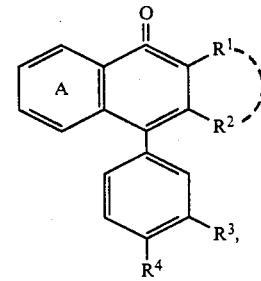

wherein R¹ and R² are a lower alkoxycarbonyl group or both may combine to form a group of the formula wherein $R^1$ and $R^2$ are a lower alkoxycarbonyl group or both may combine to form a group of the formula

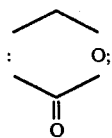

one of $R^3$ and $R^4$ is hydrogen atom or a lower alkoxy group and the other is a lower alkoxy group; ring A is a substituted or unsubstituted benzene ring, or a pharmaceutically acceptable salt thereof, which comprises the steps of:

A. treating a protected oxy-tetrahydronaphthalene compound of the formula:

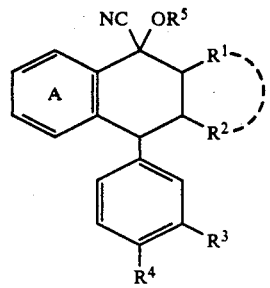

wherein $R^5$ is a protecting group for a hydroxy group; $R^1$, $R^2$, $R^3$, $R^4$ and ring A are the same as defined above, or a salt thereof with a fluorine ion-donor, to give an oxotetrahydronaphthalene compound of the formula:

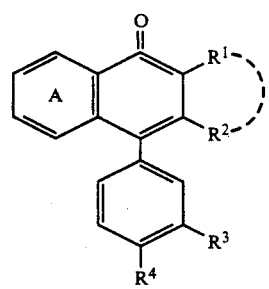

wherein $R^1$, $R^2$, $R^3$, $R^4$ and ring A are the same as defined above,

B. oxidizing the above oxo-tetrahydronaphthalene compound, an enol-form tautomer thereof or a salt thereof, C. if required, further converting the product into a pharmaceutical acceptable salt thereof.

3. A process for preparing a naphthalene derivative of the formula:

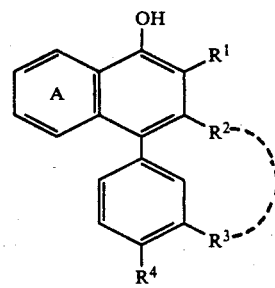

wherein $R^1$ and $R^2$ are a lower alkoxycarbonyl group or both may combine to form a group of the formula

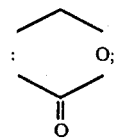

one of $R^3$ and $R^4$ is hydrogen atom or a lower alkoxy group and the other is a lower alkoxy group; ring A is a substituted or unsubstituted benzene ring, or a pharmaceutically acceptable salt thereof, which comprises the steps of:

A. reacting three compounds of the formulae:

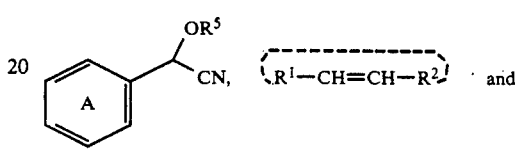

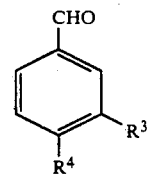

wherein $R^5$ is a protecting group for a hydroxy group, and $R^1$, $R^2$, $R^3$, $R^4$ and ring A are the same as defined above, B. further treating the product with an acid to give a protected oxy-tetrahydronaphthalene compound of the formula:

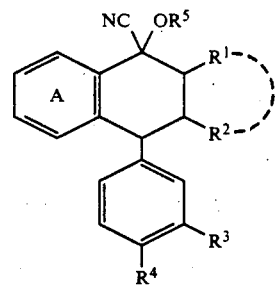

wherein $R^1$, $R^2$, $R^3$, $R^4$, $R^5$ and ring A are the same as defined above, C. treating the above product or a salt thereof with a fluorine ion-donor to give an oxo-tetrahydronaphthalene of the formula:

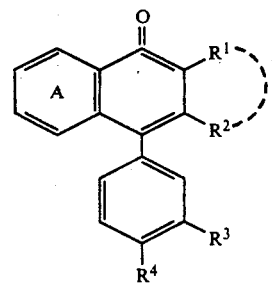

wherein $R^1$, $R^2$, $R^3$, $R^4$ and ring A are the same as defined above,

D. oxidizing the above oxo-tetrahydronaphthalene compound, an enol-form tautomer or a salt thereof, E. if required, converting the product into a pharmaceutically acceptable salt thereof.

4. A process according to claim 1 wherein ring A is an unsubstituted benzene ring; a lower alkylenedioxy group-substituted benzene ring; or a benzene ring substituted by 1-3 groups selected from the group consisting of a lower alkoxy group, a lower alkyl group, a phenyl-lower alkoxy group, hydroxy group and a halogen atom.

5. A process according to claim 4 wherein $R^1$ and $R^2$ are a lower alkoxycarbonyl group; $R^3$ and $R^4$ are a lower alkoxy group; ring A is a substituted benzene ring of the formula:

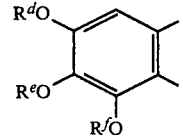

(wherein $R^d$, $R^e$ and $R^f$ are a lower alkyl group).